US011399730B2

(12) United States Patent
Miyazaki et al.

(10) Patent No.: US 11,399,730 B2
(45) Date of Patent: Aug. 2, 2022

(54) SYSTEM AND METHOD FOR NON-CONTRAST MYOCARDIUM DIAGNOSIS SUPPORT

(71) Applicant: Toshiba Medical Systems Corporation, Tochigi (JP)

(72) Inventors: Mitsue Miyazaki, Des Plaines, IL (US); Tsutomu Hoshino, Palm Harbor, FL (US); Xiangzhi Zhou, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 1088 days.

(21) Appl. No.: 15/078,691

(22) Filed: Mar. 23, 2016

(65) Prior Publication Data
US 2017/0273577 A1 Sep. 28, 2017

(51) Int. Cl.
*A61B 5/00* (2006.01)
*G01R 33/563* (2006.01)
(Continued)

(52) U.S. Cl.
CPC .......... *A61B 5/0263* (2013.01); *A61B 5/0044* (2013.01); *A61B 5/055* (2013.01); *A61B 5/318* (2021.01); *A61B 5/7203* (2013.01); *A61B 5/7282* (2013.01); *A61B 5/742* (2013.01); *A61B 5/7485* (2013.01); *G01R 33/5608* (2013.01); *G01R 33/56366* (2013.01); *G06T 7/0016* (2013.01); *A61B 5/7257* (2013.01); *A61B 5/7267* (2013.01); *A61B 5/7285* (2013.01);
(Continued)

(58) Field of Classification Search
CPC ..................................................... A61B 5/055
See application file for complete search history.

(56) References Cited

U.S. PATENT DOCUMENTS

2010/0041982 A1\* 2/2010 Kitane ................... A61B 5/055
600/419
2011/0071382 A1\* 3/2011 Miyazaki ........... G01R 33/5635
600/413

(Continued)

OTHER PUBLICATIONS

Tavares et al. (2010). Changes in Perfusion-Weighted Magnetic Resonance Imaging after Carotid Angioplasty with Stent. Interventional Neuroradiology, 16: 161-169 (Year: 2010).*

(Continued)

*Primary Examiner* — Angela M Hoffa
*Assistant Examiner* — Younhee Choi
(74) *Attorney, Agent, or Firm* — Oblon, McClelland, Maier & Neustadt, L.L.P.

(57) ABSTRACT

Devices and methods are provided for analyzing images from a magnetic resonance (MR) system. The device includes at least one hardware processor coupled with a storage system accessible to the at least one hardware processor. The device further includes a display in communication with the at least one hardware processor. The device receives a plurality of non-contrast MR images in a region of interest (ROI). The device obtains blood flow signals from the plurality of non-contrast MR images. The device identifies an abnormal segment by analyzing the blood flow signals. The device displays the non-contrast MR images by a highlighted segment in at least one of the non-contrast MR images to indicate the abnormal segment on the display.

7 Claims, 17 Drawing Sheets

(51) Int. Cl.
*A61B 5/055* (2006.01)
*G06T 7/00* (2017.01)
*G06T 7/11* (2017.01)
*A61B 5/026* (2006.01)
*G01R 33/56* (2006.01)
*A61B 5/318* (2021.01)

(52) U.S. Cl.
CPC .... *A61B 2576/023* (2013.01); *G01R 33/5602* (2013.01); *G01R 33/56308* (2013.01); *G06T 7/11* (2017.01); *G06T 2207/10016* (2013.01); *G06T 2207/10088* (2013.01); *G06T 2207/30048* (2013.01); *G06T 2207/30104* (2013.01)

(56) References Cited

U.S. PATENT DOCUMENTS

| | | | | |
|---|---|---|---|---|
| 2012/0063656 | A1* | 3/2012 | Jao | G06T 3/0068 382/128 |
| 2012/0078085 | A1* | 3/2012 | Xue | A61B 5/055 600/420 |
| 2014/0050379 | A1* | 2/2014 | Miyazaki | G06T 7/0016 382/131 |

OTHER PUBLICATIONS

Japanese Office Action dated Jul. 13, 2021, issued in Japanese Patent Application No. 2017-058270 (with English translation).

\* cited by examiner

Before Registration

After Registration

Segmentation on Tag-on or Tag-off images

Apply the ROI on the subtracted images

Non-myocardial signal removed

Segmentation with arrow indicating the landmark between LV and RV, performed on Tag-off images The segmentation ROIs are then applied on the subtracted images, each segment can be labeled with number

| The Signal Intensity of each segment can be averaged and re-displayed in gray scale | Color map can be applied on the averaged gray scale images |

Slice # illustrated in radial bull's eye direction

SYSTEM AND METHOD FOR NON-CONTRAST MYOCARDIUM DIAGNOSIS SUPPORT

TECHNICAL FIELD

The subject matter described below relates generally to magnetic resonance imaging (MRI) apparatus and process. In particular, the MRI apparatus and method described below provide non-contrast dynamic MRI myocardial perfusion analysis and visualization.

SUMMARY

In a first aspect of the present disclosure, there is provided a device for analyzing images from an MR system. The device includes at least one hardware processor coupled with a storage system accessible to the at least one hardware processor. The device further includes a display in communication with the at least one hardware processor. The device receives a plurality of non-contrast MR images in a region of interest (ROI). The device obtains blood flow signals from the plurality of non-contrast MR images. The device identifies an abnormal segment by analyzing the blood flow signals. The device displays the non-contrast MR images by a highlighted segment in at least one of the non-contrast MR image to indicate the abnormal segment on the display.

In a second aspect of the present disclosure, there is provided a method. In the method, an MR system obtains raw data by applying tag-on and tag-off data acquisition sequences in a region of interest (ROI). The MR system reconstructs a plurality of non-contrast MR images using the raw data in the ROI. The MR system obtains blood flow signals from the plurality of non-contrast MR images. The MR system identifies an abnormal segment by analyzing the blood flow signals. The MR system displays the non-contrast. MR images in a pop-up window by a highlighted segment in at least one non-contrast MR image to indicate the abnormal segment on the display.

In a third aspect of the present disclosure, a system includes a MR scanner configured to obtain raw data by applying tag-on and tag-off data acquisition sequences in an ROI. The system further includes one or more processors coupled with the MR scanner. The one or more processors are configured to: receive a plurality of non-contrast MR images in the ROI; obtain blood flow signals from the plurality of non-contrast MR images; identify an abnormal segment by analyzing the blood flow signals; highlight a segment in at least one of the non-contrast MR image; and display the highlighted segment in the at least one non-contrast MR image in a pop-up window to indicate the abnormal segment on the display.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments consistent with the invention and, together with the description, serve to explain the principles of the invention.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the invention. Instead, they are merely examples of apparatuses and methods consistent with aspects related to the invention as recited in the appended claims.

Reference throughout this specification to "one embodiment," "an embodiment," "exemplary embodiment," or the like in the singular or plural means that one or more particular features, structures, or characteristics described in connection with an embodiment is included in at least one embodiment of the present disclosure. Thus, the appearances of the phrases "in one embodiment" or "in an embodiment,"

"in an exemplary embodiment," or the like in the singular or plural in various places throughout this specification are not necessarily all referring to the same embodiment. Furthermore, the particular features, structures, or characteristics in one or more embodiments may be combined in any suitable manner.

The terminology used in the description of the disclosure herein is for the purpose of describing particular examples only and is not intended to be limiting of the disclosure. As used in the description of the disclosure and the appended claims, the singular forms "a," "an," and "the" are intended to include the plural forms as well, unless the context clearly indicates otherwise. Also, as used in the description herein and throughout the claims that follow, the meaning of "in" includes "in" and "on" unless the context clearly dictates otherwise. It will also be understood that the term "and/or" as used herein refers to and encompasses any and all possible combinations of one or more of the associated listed items. It will be further understood that the terms "may include," "including," "comprises," and/or "comprising," when used in this specification, specify the presence of stated features, operations, elements, and/or components, but do not preclude the presence or addition of one or more other features, operations, elements, components, and/or groups thereof.

It should be understood, although elements may be described as terms first, second, third or the like in the present disclosure, the elements are not limited by these terms. Rather, these terms are merely used for distinguishing elements of the same type. For example, a first element can also be referred to as a second element, and similarly, a second element can also be referred to as a first element, without departing from the scope of the present disclosure. Depending on the context, as used herein, the word "if" can be interpreted as "at the time when", "when" or "in response to."

Figure 1:
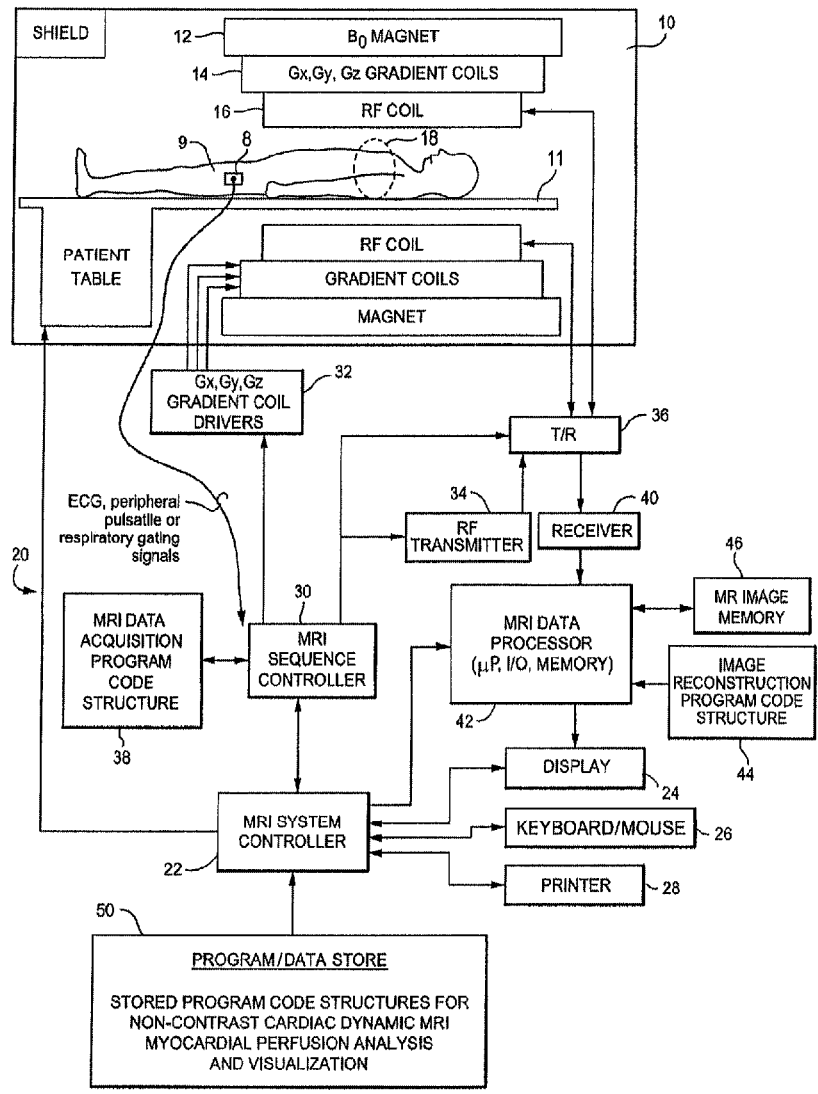
FIG. 1 is a high-level schematic block diagram of an exemplary MRI system configured to provide non-contrast dynamic MRI myocardial perfusion analysis and visualization.

The MRI system shown in FIG. 1 includes a gantry 10 (shown in schematic cross-section) and various related system components 20 interfaced therewith. At least the gantry 10 is typically located in a shielded room. The MRI system geometry depicted in FIG. 1 includes a substantially coaxial cylindrical arrangement of the static field $B_0$ magnet 12, a Gx, Gy and Gz gradient coils 14 and an RF coil 16. Along the horizontal axis of this cylindrical array of elements is an imaging region 18 shown as substantially encompassing the anatomy of interest (i.e., region of interest or "ROI") for a patient 9 (e.g., the heart for cardiac MRI) supported by a patient table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls Gx, Gy and Gz gradient coil drivers 32, as well as an RF transmitter 34 and a transmit/receive switch 36 (if the same RF coil is used for both transmission and reception). As those skilled in the art will appreciate, many different types of RF coils (e.g., whole body coils, surface coils, birdcage coils, coil arrays, etc.) may be employed to transmit and/or receive RF signals to/from the ROI in the imaging volume. As will also be appreciated, one or more suitable physiological transducers 8 may be affixed to the patient's body to provide ECG (electrocardiogram), respiratory and/or peripheral pulsatile gating signals to the MRI sequence controller 30. The MRI sequence controller 30 also has access to suitable MRI data acquisition program code structure 38 for implementing MRI data acquisition sequences already available in the repertoire of the MRI sequence controller 30—e.g., to generate non-contrast cardiac MRI tissue images using operator and/or system inputs defining particular MRI data acquisition sequence parameters, one or more ROI, etc.

The MRI system 20 includes an RF receiver 40 providing input to MRI data processor 42 so as to create processed image data which may be sent to the display 24. The MRI data processor 42 is also configured for access to image reconstruction program code structure 44 and to MR (magnetic resonance) image memory 46 (e.g., for storing MR image data derived from processing in accordance with the exemplary embodiments and the image reconstruction program code structure 44).

The MRI data processor 42 is configured to receive a plurality of non-contrast MR images in a region of interest (ROI). The MRI data processor 42 is configured to obtain blood flow signals from the plurality of non-contrast MR images. For example, the MRI data processor 42 may subtract the tagged image corresponding to the tag-on pulse sequence from the normal image corresponding to the tag-off pulse sequence and obtains a difference image, which includes the blood flow signals.

The MRI data processor 42 is configured to identify an abnormal segment by analyzing the blood flow signals. For example, the MRI data processor 42 may identify a plurality of segments in each of the plurality of non-contrast MR images. The MRI data processor 42 may generate a curve as a function of a time parameter for each segment, the curve indicating blood perfusion information in each segment. The MRI data processor 42 may calculate an area under the curve before and after a treatment to the abnormal segment. The treatment may include revascularized techniques such as stent insertions into blood vessels, surgical bypass blood vessel operations, etc.

The MRI data processor 42 is configured to display the non-contrast MR images by superimposing a highlighted segment in at least one of the non-contrast MR image onto at least one non-contrast MR images to indicate the abnormal segment on the display. The MRI data processor 42 thus makes the operator to pay more attention to the highlighted segment in the at least one of the non-contrast MR images. The highlighted segment may also be color coded to indicate the severities and/or types of the condition. The MR data processor 42 may further display a pop-up window adjacent to the highlighted segment, where the pop-up window may include confidence level and/or other information to help the operator understand the condition of the patient. For example, the MRI data processor 42 may display the non-contrast MR images with a highlighted segment and a small pop-up window on the display 24 or any other display devices. The MRI data processor 42 may further display one or more arrows of different colors adjacent to the highlighted segment, where the color may indicate the severities and/or types of the condition.

Also illustrated in FIG. 1 is a generalized depiction of an MRI system program/data store 50 where stored program code structures (e.g., for non-contrast cardiac MRI dynamic myocardial perfusion analysis and visualization), as well as a related graphical user interface (GUI), operator inputs to same, etc., which are stored in computer readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those skilled in the art will appreciate, the FIG. 1 depiction is a very high-level simplified diagram of a typical MRI system with some modifications so as to practice exemplary embodiments to be described herein below. The system components can be divided into different logical collections of "boxes" and typically comprise numerous digital signal processors (DSP), microprocessors, special purpose processing circuits (e.g., for fast ND conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR imaging reconstruction process, an array of computer-readable accessible data value storage sites (e.g., multi-digit binary representations of pixel values) in physical storage media will be transformed from some prior state (e.g., all uniform "zero" values or all "one" values) to a new state wherein the physical states at the physical sites of such an array (e.g., of pixel values) vary between minimum and maximum values to represent real world physical events and conditions (e.g., the tissues of a patient over an imaged region space). As those in the art will appreciate, such arrays of stored data values represent and also constitute a physical structure—as does a particular structure of computer control program codes that, when sequentially loaded into instruction registers and executed by one or more CPUs of the MRI system 20, cause a particular sequence of operational states to occur and be transitioned through within the MRI system.

The exemplary embodiments described below provide improved ways to acquire and/or process MRI data acquisitions and/or to generate and display MR images.

Use of an injected gadolinium (Gd)-based contrast agent (possibly in association with an injected stress perfusion agent) is known, but use of such contrast agents is often not an acceptable MRI technique for detecting infarct and ischemic lesions in myocardium. Late gadolinium contrast enhancement (LGE) is based on measuring a difference between normal and infarct myocardium by observing MRI T1-contrast (wash-out) of the gadolinium contrast agent via observed MRI signals from the myocardium after injection. In order to obtain a realistic observation of myocardium under stress, such stress may be induced by patient physical exercise or injected drug-induced stress (intended to cause increase in heart rate, dilation of cardiovascular blood vessels, etc., similar to that caused by physical exercise) so as to hopefully better observe blood flow abnormalities under such transient stress situations.

Arterial Spin Labeling (ASL) has also been used for non-contrast myocardial ischemia evaluation, but this technique has been limited to a single slice at a single time point without the capability to generate perfusion curves or three-dimensional (3D) coverage. The corresponding analysis method is considerably different from our new non-contrast dynamic MRI perfusion analysis and visualization.

In particular, we have now discovered a way to avoid use of such contrast agents by achieving a non-contrast (i.e., without injection of a chemical contrast agent) MRI technique for producing myocardium perfusion curves/table data that can be used to distinguish between normal myocardium, ischemic myocardium and infarct myocardium. Indeed, even revascularized infarct myocardium (treated with revascularized techniques such as stent insertions into blood vessels, surgical bypass blood vessel operations, etc.) may be distinguished. In accordance with exemplary embodiments, such myocardium distinctions can be made within any desired region of interest (e.g., an operator-defined arbitrary region of interest, a standard American Heart Association (AHA) segment, a single pixel, etc.).

Although injection of a contrast agent (e.g., gadolinium-based) is avoided, it may still be desirable to use exemplary embodiments in combination with patient stress (either exercise-induced or drug-induced) so as to better detect abnormalities that may exist or be more prominent only during such stressed situations.

In exemplary embodiments, a set of "tag-on" (2D or 3D) MRI k-space data is acquired after an incoming volume of blood has been "tagged" with an initial spatially selective RF pulse (e.g., typically a spatially selective 180° inversion pulse) where the data acquisition subsequence starts after a given inversion time (TI) delay interval. A similar set of "tag-off" MRI data is also acquired using the same TI delay interval—but without the initial spatially selective RF tagging pulse. This technique is sometimes known in the art as black blood time to inversion (BBTI) imaging. A sequence of such tag-on/tag-off data sets for each of plural TI times is acquired in k-space.

For each given TI time, 2D/3D Fourier Transform reconstructed spatial domain tag-on and tag-off image data sets (i.e., the result of well-known 2DFT/3DFT reconstruction processes) are subtracted (e.g., on a pixel-by-pixel basis) to provide BBTI blood perfusion images where blood perfusion (MR signal strength) as a function of time can be plotted or tabulated. For any given region of interest (e.g., an AHA segment, arbitrary operator-defined ROI or even a single pixel), a plot of the time sequence of data values provides a blood perfusion curve as a function of time which provides several dimensions of differentiation between perfusion curves for "normal" myocardium, abnormal ischemic myocardium, infarct myocardium—and even revascularized (treated) ischemic myocardium. As will be expected, infarct myocardium shows no perfusion (i.e., no peak or increase in detected MRI signal strength). However, ischemic myocardium has a time-delayed peak flow time of occurrence, as well as less detected signal intensity, when compared to normal (or revascularized) myocardium. Accordingly, ischemic areas may be distinguished based upon time and/or amplitude (or even integrated area under the curve) comparisons and/or comparisons to predetermined thresholds, etc.

For example, the MRI data processor 42 may analyze non-contrast MR images from patients and healthy volunteers to determine one or more thresholds. The MRI data processor 42 is configured to obtain a first threshold value corresponding to a peak blood flow in a normal tissue in an organ by receiving an input from an operator based on analyzing the non-contrast MR images of patients. The first threshold value may be arbitrary for each patient and the operator may need to be professionally trained to determine the input by analyzing the non-contrast images. The MRI data processor 42 is further configured to obtain a second threshold value corresponding to when the peak blood flow occurs in the normal tissue in the organ by analyzing non-contrast MR images corresponding to data from healthy subjects or patient with healthy tissues.

The MRI data processor 42 is configured to identify an abnormal segment by comparing the obtained blood flow signals to a threshold value corresponding to normal tissue in an organ. For example, the MRI data processor 42 may obtain the threshold value corresponding to the lowest blood flow in normal tissues of left ventricle in the heart. The MRI data processor 42 may also obtain the threshold value corresponding to the average blood flow in normal tissue of left ventricle in the heart. Using one or more of the threshold values, the MRI data processor 42 may identify the abnormal segment when the obtained blood flow signals are lower than the threshold value in one or more regions.

The MRI data processor 42 is configured to obtain a first plurality of blood flow signals corresponding to a region including abnormal tissue in an organ before a treatment procedure to restore perfusion in the region. The MRI data processor 42 may obtain the first plurality of blood flow signals using the non-contrast MR images before the treatment procedure so that the doctors or other operators understand the risk and condition of the patient's condition. Further, the doctors may use the first plurality of blood flow signals as baseline images for evaluation of the treatment.

The MRI data processor 42 is configured to obtain a second plurality of blood flow signals corresponding to the region including abnormal tissue in the organ after the treatment procedure. The MRI data processor 42 may analyze the non-contrast MR images in the same ROI before the treatment procedure. The MRI data processor 42 is configured to determine whether the treatment procedure is successful by comparing the first plurality of blood flow signals and the second plurality of blood flow signals.

For example, the MR data processor 42 may determine that the treatment procedure is successful when the second plurality of blood flow signals indicate that a peak blood flow in the region is greater than a first threshold, which may be referred as the first condition. The MR data processor 42 may determine that the treatment procedure is successful when a peak time corresponding to the peak blood flow is less than a second threshold, which may be referred as the second condition. The MR data processor 42 may assign different weights to the above two conditions so that the final determination may consider both the difference in the peak blood flow and the difference in the corresponding peak time.

A perfusion curve and/or a corresponding data table pertaining to a region of interest (e.g., a predetermined AHA myocardium segment or an arbitrary operator-indicated ROI or even a single pixel) that includes distinguishing characteristics so that the MRI results (e.g., as displayed to an operator or stored data for later display to others) can differently depict the ROI as representing normal, ischemic, infarct or even revascularized myocardium—all without use of any injected contrast agent (e.g., gadolinium).

Figure 2:
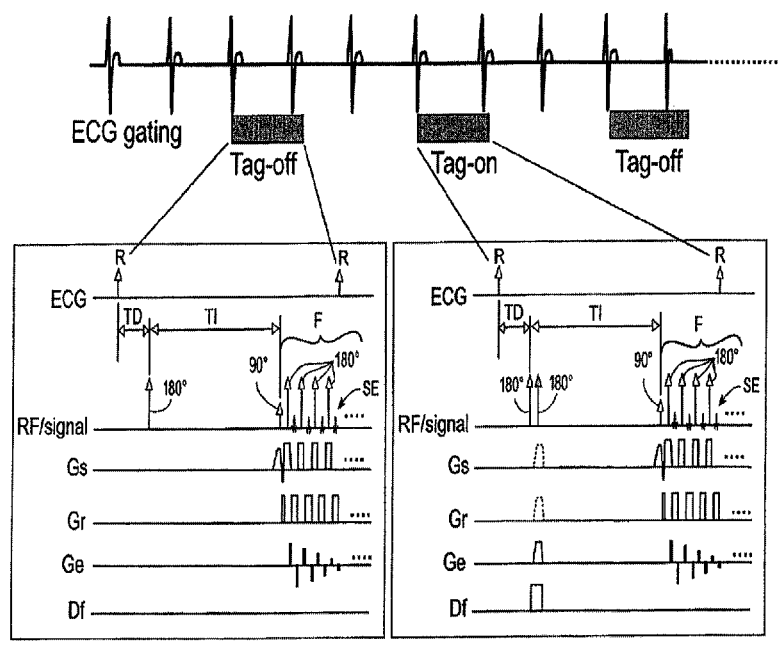
FIG. 2 is a schematic depiction of a first exemplary tag-on, tag-off MRI data acquisition sequence for use in the system of FIG. 1.

In an exemplary data acquisition sequence depicted at FIG. 2, electrocardiogram (ECG) gating is used so as to synchronize both "tag-off" and "tag-on" subsequences as depicted. In the tag-off subsequence shown to the left-lower side of FIG. 2, a short initial fixed time delay TD is employed to ensure that the data acquisition subsequence begins its active phase during a desired diastole portion of the RST ECG signal. After the delay TD, a non-selective 180° nuclear magnetic resonance (NMR) RF nutation pulse is employed (to help suppress background signals from a subsequent difference image because the signal from myocardium is relatively small, e.g., about 10% of the total MRI signal). The active phase of the actual data acquisition subsequence may, if desired, begin with a preparation pulse (e.g., a fat suppression pulse), followed by a desired data acquisition subsequence F initiated with a slice-selective (e.g., $\alpha°$—typically 45° or 90°) NMR nutation pulse to initiate a desired MRI data acquisition subsequence F, e.g., a sequence of slice-selective 180° RF nutation refocusing pulses to elicit intervening RF spin echo (SE) responses during readout gradient Gr pulses, each spin echo being preceded by a phase encoding Ge magnetic gradient pulse (which is varied for different echoes so as to elicit date for a respectively corresponding line in k-space). As those in the art will appreciate, such known MRI data acquisition subsequences might be, e.g., of the balanced steady-state free precession (bSSFP) type (presently preferred) or of the fast spin echo (FSE) type or possibly of other types.

The tag-on data acquisition subsequence depicted at the right-lower side of FIG. 2 is similar to the tag-off subsequence—except that, after the delay TD, there is also a spatially selective "tagging" 180° RF nutation pulse (e.g., perhaps at an oblique angle as represented by the dotted concurrent gradient pulses and the frequency offset pulse Df as depicted). As those in the art will appreciate, this will, in effect, revert a predetermined inflowing volume of blood back to a non-inverted magnetization orientation—thus "tagging" this inflowing volume of blood so that it will generate different MR signal responses from those for the tag-off subsequence as the RF tagged flowing blood MR nuclei enter into the downstream ROI.

Figure 3:
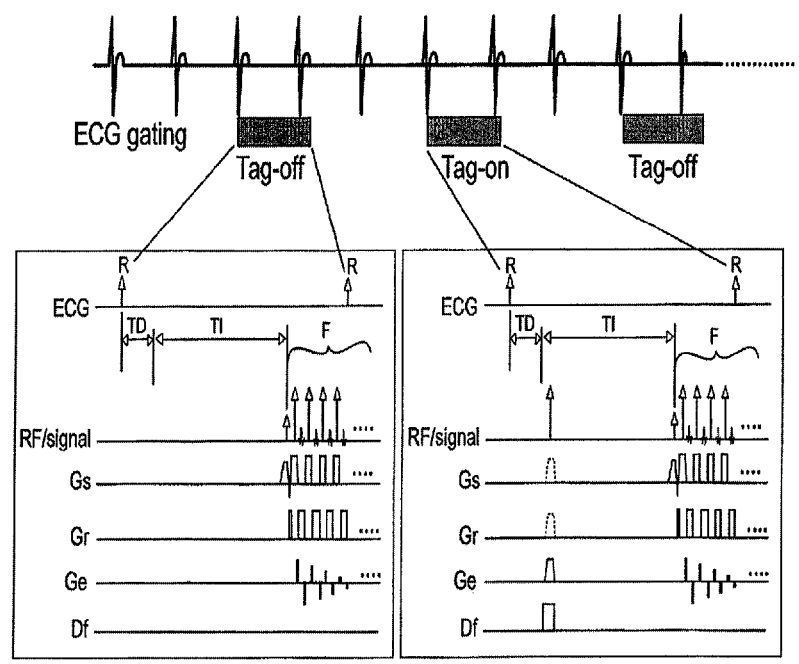
FIG. 3 is a schematic depiction of a second exemplary tag-on, tag-off MRI data acquisition sequence for use in the system of FIG. 1.

The tag-on/tag-off alternate acquisition subsequences depicted in FIG. 3 are the same as those depicted in FIG. 2, except that, as will be observed, there is no initial non-selective 180° nutation pulse (in either tag-on or tag-off subsequences) for background suppression purposes.

As depicted in the dotted lines in both FIGS. 2 and 3, to achieve a desired oblique orientation for the spatially selective 180° tag-on nutation pulse, there may be concurrent usage of differently chosen magnitudes Gs, Gr and Ge magnetic gradient pulses.

Exemplary analysis methods are provided for use with the above non-contrast dynamic myocardial perfusion techniques. For example, the new methods may process a dynamic, 3D image data set with the capability to visualize blood perfusion in the left ventricle (LV) and to show perfusion curves for any segments or ROI defined by the user.

As will be understood by those in the art, the perfusion analysis and visualization methods may be incorporated into the MRI system of FIG. 1. Alternatively or additionally, the perfusion analysis and visualization methods may be implemented as part of a separate image analysis/display system remotely located from the MRI system of FIG. 1 where original tag-on and tag-off image data are acquired.

For dynamic 3D images obtained from our non-contrast perfusion techniques, we propose the following exemplary presented preferred analysis procedures (not all of which may always be required or desired):

1. Perform complex data subtraction between tag-on and tag-off images.
2. Perform image registration: rigid or non-rigid registration for 3D images at different BBTIs.
3. Create histograms of tag-on and tag-off images to check for myocardium signal loss caused by susceptibility and/or by the tagging slice affecting the imaged slice. By subtraction of the histograms, adverse susceptibility and tagging slice effects on the imaged myocardium can be detected.

4. Use myocardial segmentation.

5. Display the segmented myocardium in a color map format.

6. Create a perfusion curve for each segment or ROI across all slices.

7. Concurrently display all 3D slices versus BBTI.

8. Concurrently automatic display respectively corresponding perfusion curves when selecting a segment and/or ROI.

9. Perfusion curve fitting quantification purposes.

Figure 4:
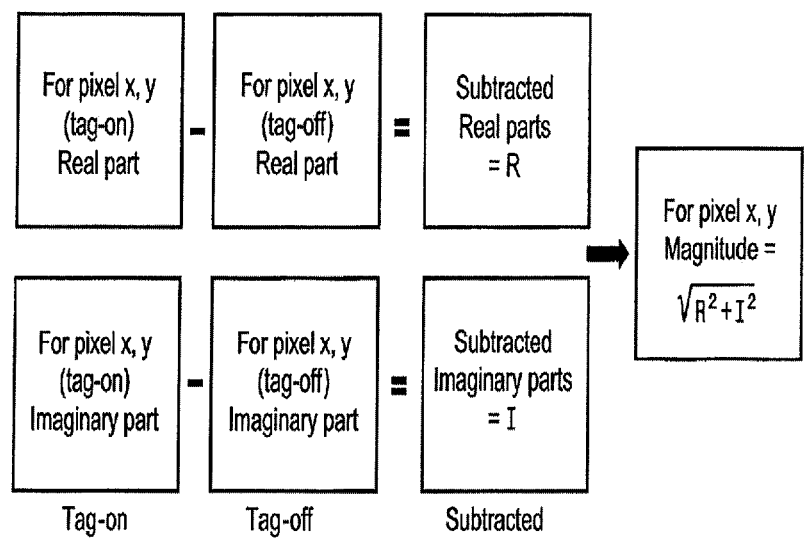
FIG. 4 illustrates subtraction of previously acquired tag-on and tag-off images on a pixel-by-pixel basis using complex-valued arithmetic so as to produce a magnitude image of the subtracted tag-on and tag-off images.

Complex data subtraction of the tag-on and tag-off image data is depicted in FIG. 4. The subtracted image should be in complex format (real and imaginary parts, R+jI) because the magnitudes of subtracted pixels are then made insensitive to signal changes caused by possible phase shifts between tag-on and tag-off signals. Thus, the original tag-on and tag-off images should also be in complex-valued format. The complex-valued data after subtraction is then used to build a magnitude image for perfusion analysis.

Figure 5A:
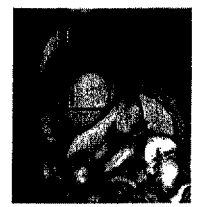
FIGS. 5A and 5B illustrate left ventricle (LV) magnitude images (e.g., resulting from the process of FIG. 4) at different BBTI periods both before registration and after registration.
Figure 5B:

Since the 3D images at different BBTIs are acquired at different acquisition times, registration between different BBTI images may be necessary. The example images in FIGS. 5A and 5B demonstrate the 3D registration for an imaging slab across all BBTIs (for simplicity in explanation, only one slice is shown).

Registration is not limited to rigid registration. For example, the donut shape of a left ventricle cross-section at one BBTI may have a slightly different shape at another BBTI. In this case, non-rigid registration should be performed.

Since it is desired to register the left ventricle (LV), in the proposed exemplary method, a regional registration for the LV can be performed if the registration window is placed on the LV only. If a non-selective pulse is used, the contrast between a heart chamber and the surrounding myocardium will be inverted at some BBTIs. In this case, both tag-on and tag-off images should be utilized in the registration process. For example, one can select the images with positive contrast (myocardial signal intensity SI>LV chamber blood SI) and perform registration on those. Then one can select negative contrast images and perform another registration process. The registration shift of pixels of each image relative to the reference images can be recorded for a combined registration process. Manual shifting with a visual check may be necessary to achieve the best registration.

Figure 6A:
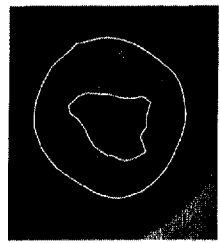
FIGS. 6A, 6B and 6C illustrate segmentation imposed on tag-on or tag-off images with the segmented region of interest (ROI) being superimposed on the subtracted images and a clear image where non-myocardial signals outside the segmented volume have been removed.
Figure 6B:
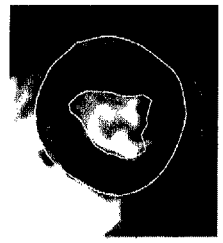
Figure 6C:
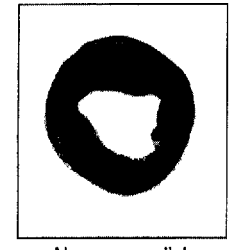

LV segmentation can be achieved after registration by aligning the LV along successive BBTI images as depicted in FIGS. 6A, 6B and 6C. On the tag-off images, the endocardial and epicardial contours may be drawn (manually or semi-automatically) for each slice and saved. Then the saved contours can be applied onto the subtracted images. To visualize LV myocardium only, other signals can be removed (e.g., see the clear" image of FIG. 6C). Note that the LV contours should be carefully placed to exclude any contamination from artifacts (e.g., susceptibility artifacts) and tagging slice interference.

Figure 7A:
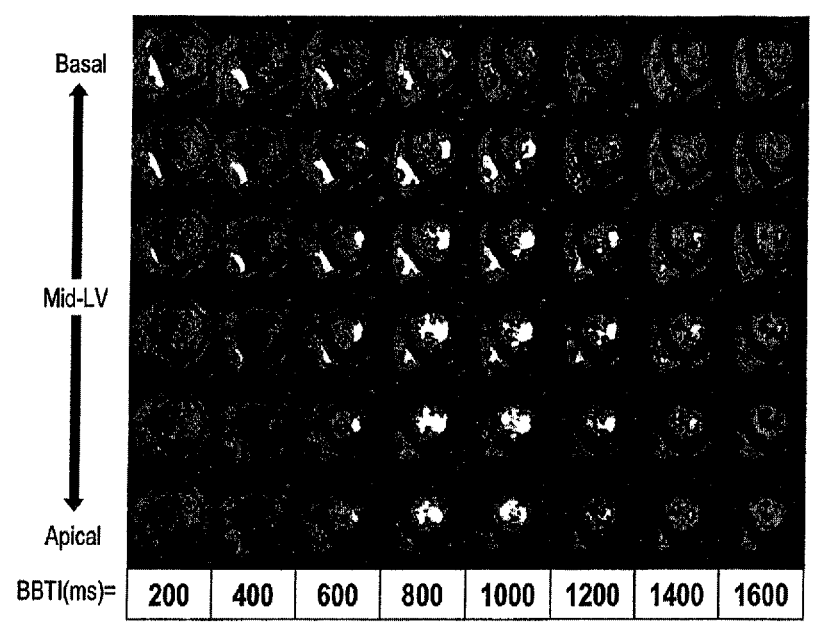
FIGS. 7A and 7B depict exemplary perfusion visualizations wherein left ventricle cross-sectional images at plural BBTI values are displayed together in one panel as a function of BBTI time periods—before LV segmentation in FIG. 7A and after segmentation in FIG. 7B.
Figure 7B:
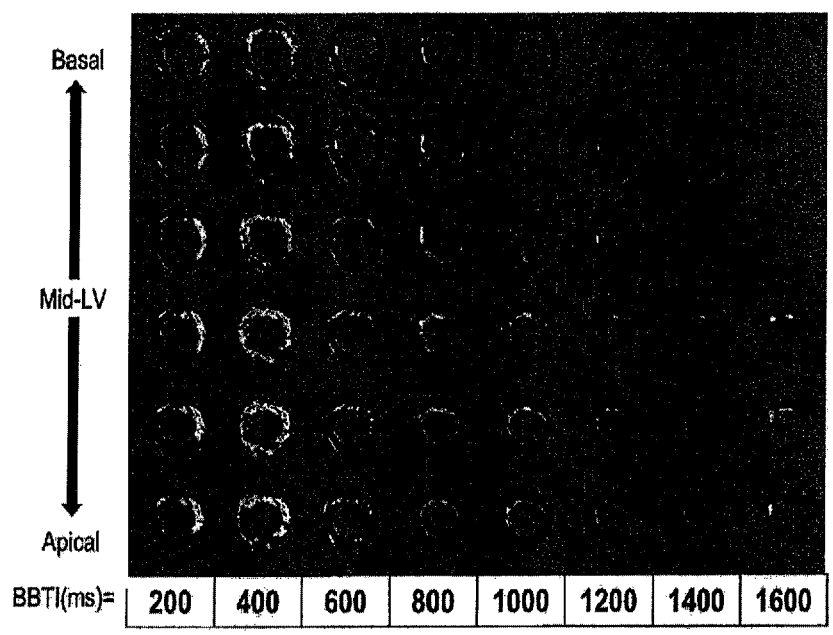

Perfusion visualization can be achieved as shown in FIGS. 7A-B. Here, LV images from apical to basal slices at all BBTIs are displayed in one panel. In this panel, the blood perfusion in the left ventricle can be observed (a colorized map is preferably applied to better visualize the signal intensity change). FIG. 7A depicts visualization before LV segmentation while FIG. 7B depicts visualization after segmentation.

Coronary artery territory segmentation in LV may, for example, be either the standard American Heart Association (AHA) six-segment model or, if desired, any number of other user-defined segmentation. The AHA six segmentation depicted in FIGS. 8A, 8B, 8C and 8D starts from the groove between LV and RV (right ventricle) and automatically runs clockwise. That is, the groove is marked as the start point to identify the coronary artery territory. Each succeeding numbered AHA segment can be labelled, averaged and color-mapped to distinguish and show intensity changes among all segments as depicted in FIGS. 8A-8D.

Figure 9A:
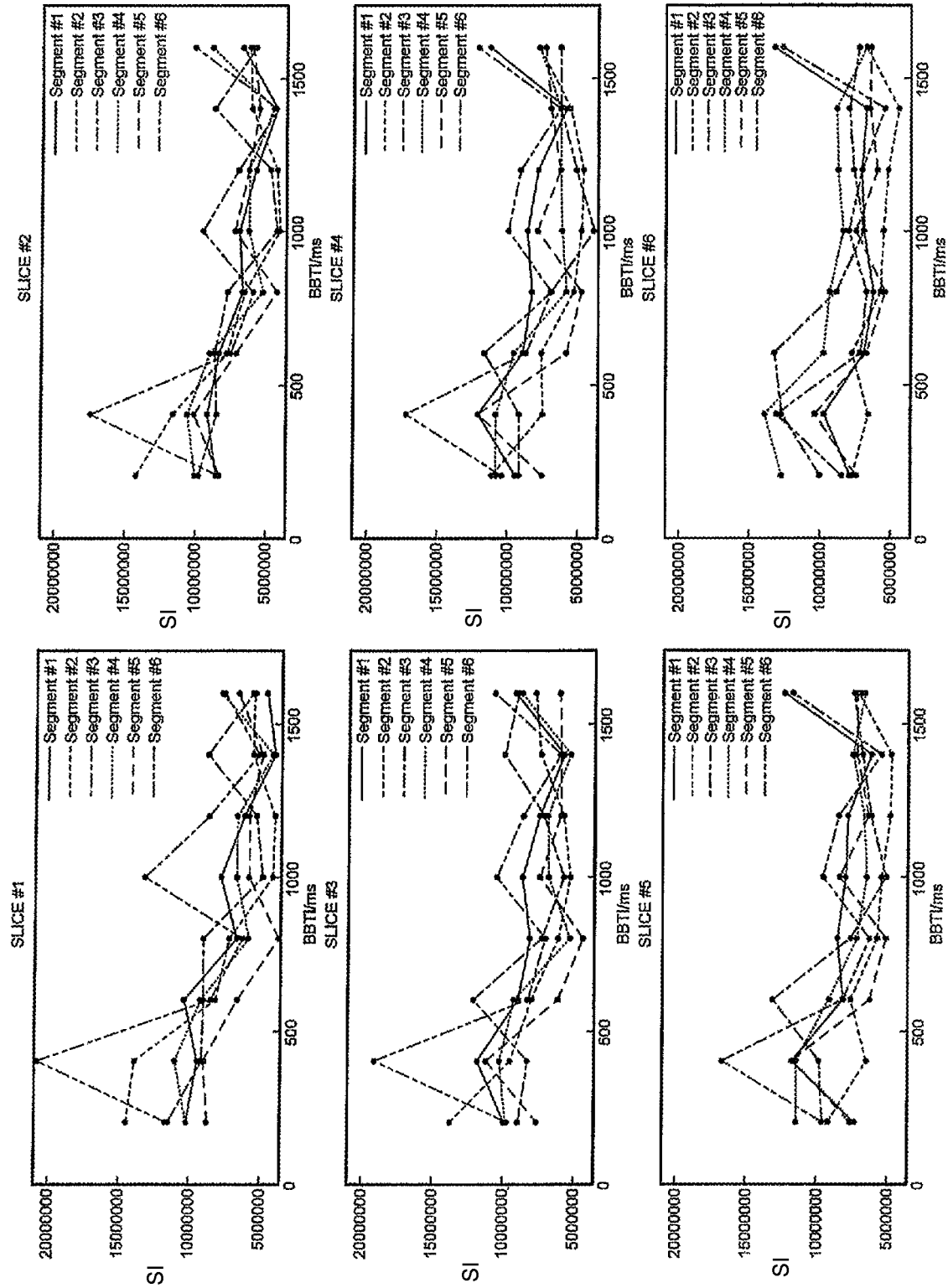
FIGS. 9A-C depict simultaneous one-panel display visualizations of perfusion curves for each segment in each of different slices as a function of BBTI parameter values using different exemplary visualization presentations.
Figure 9B:
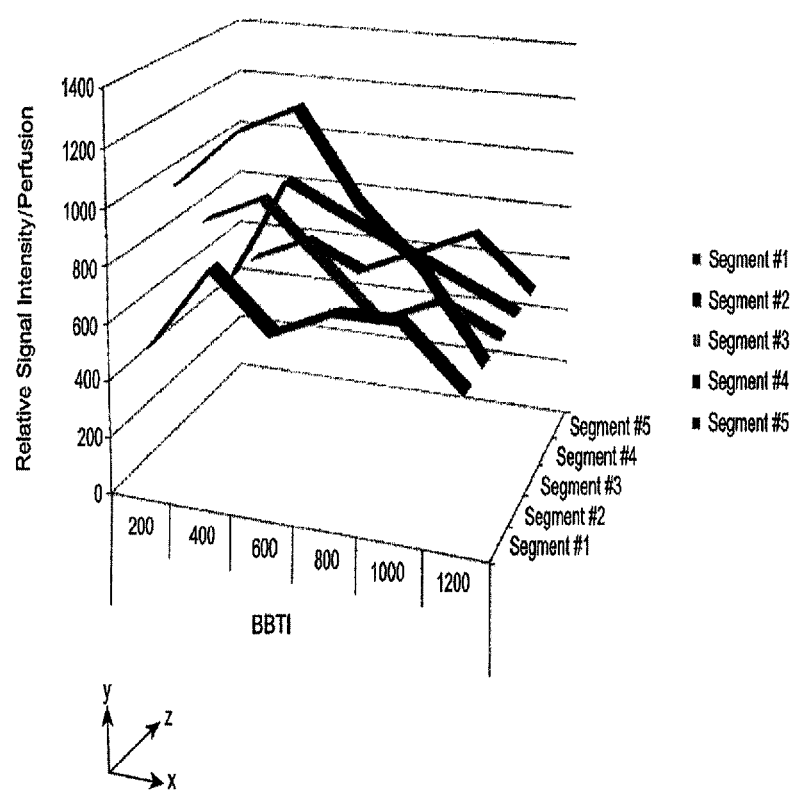
Figure 9C:
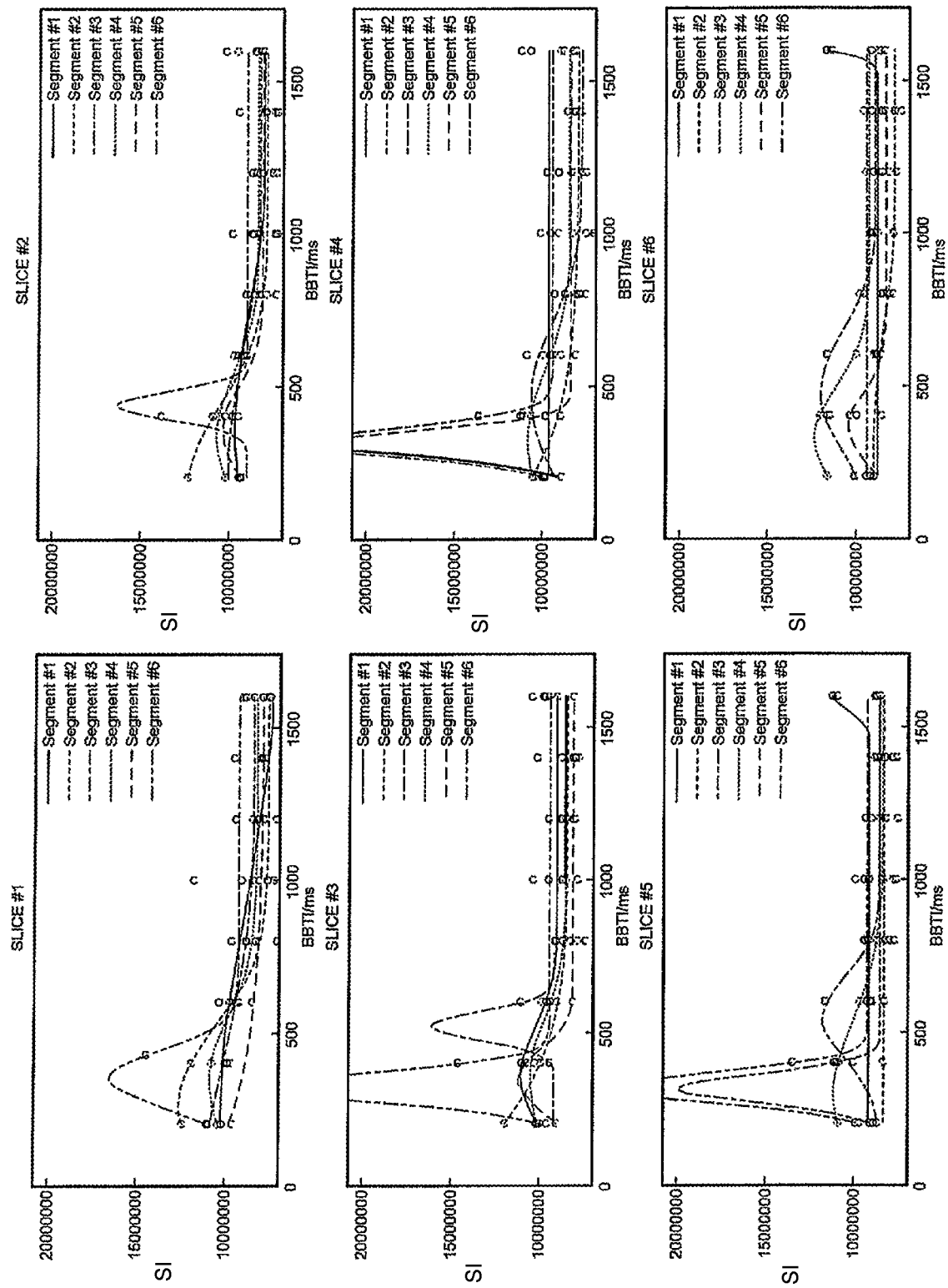

Perfusion curves of each segment in each different slice along the different BBTI images can be created as shown in FIGS. 9A-C. With the saved ROIs of all segments, the perfusion curves can be automatically generated for all segments in all slices. The FIG. 9A example shows unsmoothed raw perfusion curves from one patient. The perfusion curves can be also generated from any ROI that the user has specified.

Conventional polynomial curve fitting or curve smoothing techniques may be applied to assist in further quantification analysis as shown in FIG. 9C. Preferably, two or more curve fitting equations may be used to best fit the perfusion curves. The fitted parameters may be able to describe the perfusion peak intensity, timing of the peak, and the area under the peak. Preferably any identifiable abnormal parameters (e.g., as ascertained by quantitative analysis of the curve fitted perfusion data) should be marked in a fitted parameter table and/or directly on the displayed perfusion curves. Similarly, any region(s) corresponding to the detected abnormalities preferably should be marked directly onto the visualizations of the corresponding AHA segments. The MR system may collect data from a plurality of patients and obtain fitted parameters for all patients in the same section. Thus, the MR system may identify mean values of the fitted parameters for each section in an organ. The MR system may also obtain variance values for the parameters. The mean and variance values may be used to calculate a probability or confidence value for analysis of a particular patient organ.

FIG. 9B illustrates a simulated 3D visualization of perfusion curves where (using a typical orientation of orthogonal x,y,z coordinate axes) BBTI values are plotted with respect to an x-axis, relative signal intensity (perfusion) is plotted with respect to a y-axis and slice number is plotted with respect to a z-axis of the visualization display.

Although the perfusion curves are shown in one panel in FIGS. 9A-C, any one perfusion curve can be fetched for overlaid display in FIG. 7A or FIG. 7B when a particular respectively corresponding slice or segment is selected by a user (e.g., by "clicking" a mouse arrow when positioned over that slice or segment of a particular slice at a particular BBTI).

Figure 10A:
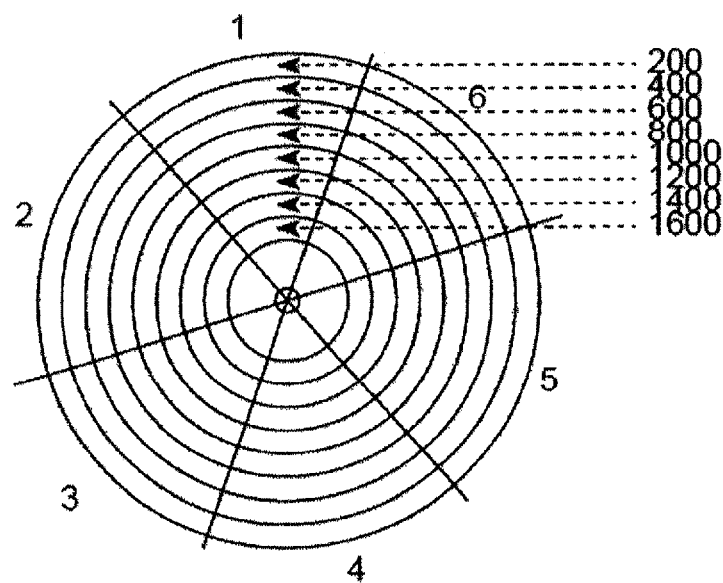
FIGS. 10A-B illustrate new types of bull's eye depictions for better visualization and understanding of relationships between BBTI, signal intensity (SI) which is related to perfusion and/or LV slice numbers constituting substantially contiguous slices within a 3D image of the LV.
Figure 10B:
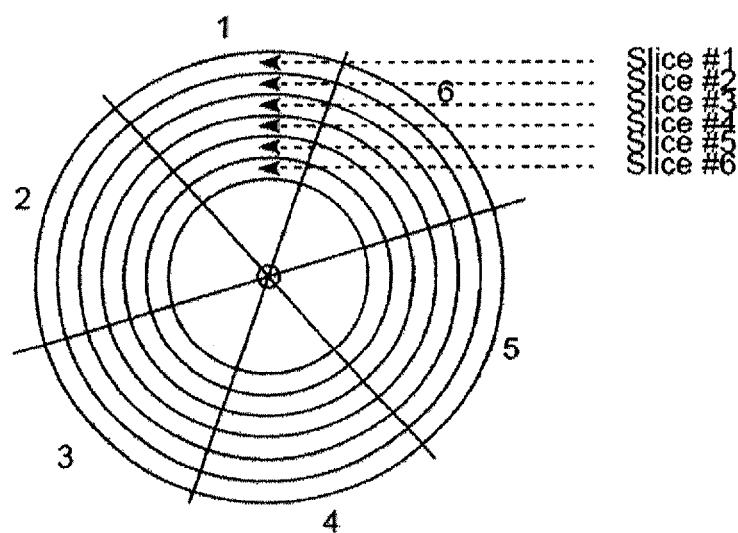

FIGS. 10A-B illustrate new perfusion visualizations using a variation of the well-known bull's eye technique. Here, in FIG. 10A, for a given slice number, concentric circles illustrate AHA segments with BBTI values being illustrated along the radial direction. Each bull's eye segment preferably is color-coded for average signal intensity (SI) or relative perfusion value. In this visualization, a trend of SI as a function of BBTI for each cardiac segment can be easily seen and understood. In FIG. 10B, for a given BBTI value, the concentric circles also illustrate AHA segments but now slice numbers are illustrated along the radial direction. Here each bull's eye segment preferably is also color-coded to represent the average SI or perfusion value—and now in this visualization, a trend of SI as a function of slice number at a given BBTI can be easily seen and understood.

The exemplary analysis methods are especially designed for use with our non-contrast dynamic myocardial perfusion techniques. The whole analysis procedure helps visualize perfusion of blood inside myocardium, and to distinguish infarcted regions or ischemic regions from healthy myocardium. The generated perfusion curves are important for quantified evaluation of ischemic disease or infarction.

Figure 11:
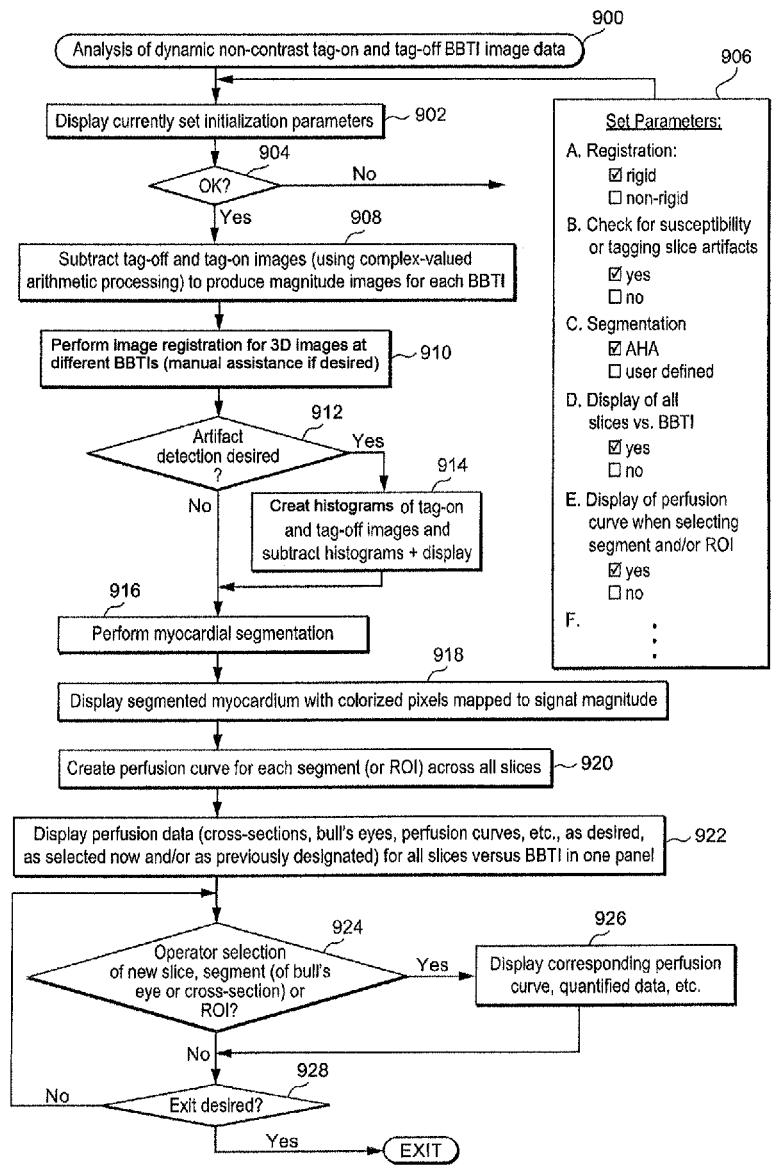
FIG. 11 is a schematic illustration of exemplary computer program code structure for use in the system of FIG. 1 (or a separate image data processing system) in the form of a flow chart for implementing exemplary embodiments of a system for analyzing BBTI tag-on and tag-off images acquired by magnetic resonance imaging (MRI)

FIG. 11 depicts entry into an analysis of dynamic non-contrast tag-on and tag-off BBTI image data at 900. As those in the art will appreciate, this flow chart represents executable computer program code structures such as found in a computer program subroutine that can be called by a higher level application program or operating system. If desired, the current (initially or last used) set initialization parameters may be displayed at 902 and, if the user is not satisfied with those (as tested at 904), then a parameter initialization screen 906 can be displayed for further operator adjustments/inputs and those will then be displayed again at 902 for acceptance or not at 904.

Once the initialization of the subroutine is found acceptable (if indeed the operator is even given an opportunity for such adjustments), then at 908, previously acquired tag-on and tag-off images are subtracted using complex-valued arithmetic data processing to produce magnitude images for each BBTI value and for each slice of a 3D image.

Subsequently, image registration may be performed at 910 for 3D images at different BBTI values. If desired, manual assistance may be permitted to effect image registration. Of course, image registration need not be required.

If artifact detection is desired as tested at 912, then histograms of tag-on and tag-off images are created at 914 and subtracted so as to provide data representing susceptibility errors and/or errors caused by a tagging pulse affecting the myocardium during image data acquisition. As those in the art will appreciate, block 914 can include tests to detect whether error above a certain threshold is present and, if so, to take remedial action and/or request operator assistance or perhaps even to terminate the process.

At block 916, myocardial segmentation may be performed, if desired. The segmented myocardium is then displayed with colorized pixels mapped to signal magnitude at 918. Perfusion curves are created for each segment (or ROI) for each slice of the 3D image at 920. The slices and/or perfusion curves may be displayed vs. BBTI values at 922. As previously discussed, the colorized slice images for the 3D image are preferably displayed in one panel as a function of BBTI values. Similarly, the perfusion curves for each segment and slice of the 3D image are preferably displayed in a single panel.

If the slices are depicted in a single panel, then at 924, an operator is given an opportunity to select a particular segment or ROI at the display (e.g., with a mouse or by touch or the like). If such an operator selection is made, then the corresponding perfusion curve for that particular segment is displayed at 926. The operator is given an option for exit at 928. If and when that desire is indicated, then this subroutine is exited at 930 and control is passed back to the calling higher level program or operating system.

Displaying multi-slice images of any type (i.e., not just perfusion-related images but also non-contrast MR images such as from magnetic resonance angiography (MRA) along a BBTI axis is believed to be new and advantageous. For example, a computerized system for analyzing images acquired by magnetic resonance (MR) imaging may include at least one computer processor coupled to associated memory, display and input/output ports and be configured to: (a) acquire multi-slice non-contrast MR images of left ventricle (LV) myocardium for each of plural BBTI intervals in a region of interest (ROI); and (b) display apical to basal LV slice images as a function of BBTI for plural slices of a 3D image and for plural BBTI values in a single display panel. Such visualization of MR slices as a function of BBTI in a single display panel (e.g., similar to visualizations shown in FIGS. 7A, 7B, 9A-C and/or 10A-B will help users to more quickly "see" important relationships between a succession of BBTI values and various types of MR images acquired with varying BBTI values.

Figure 12A:
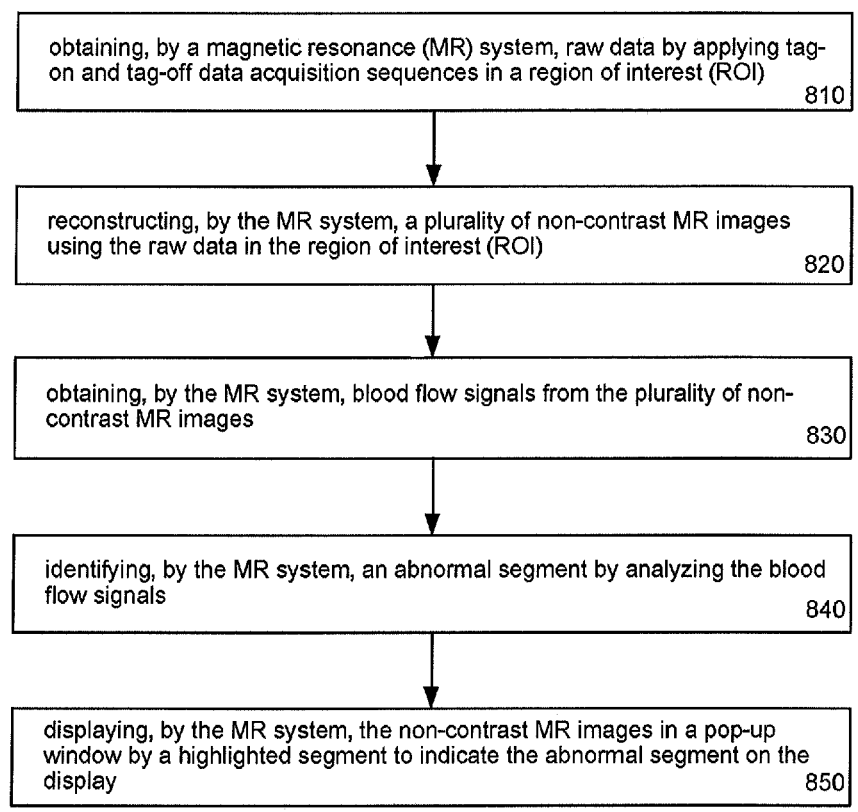
FIGS. 12A-B illustrate a method at least partially implemented by the system of FIG. 1.
Figure 12B:
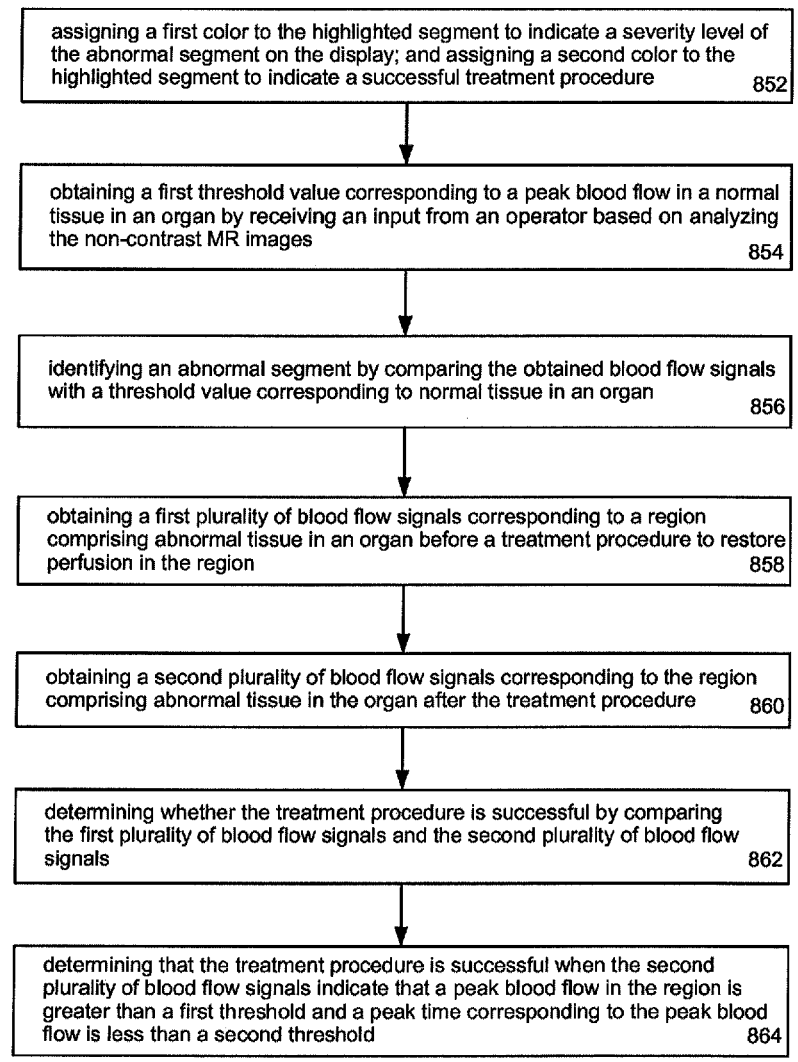

FIGS. 12A-B illustrate a method at least partially implemented by the system of FIG. 1.

In FIG. 12A, the method includes the following acts. In act 810, the MR system obtains raw data by applying tag-on and tag-off data acquisition sequences in a region of interest (ROI). The tagged slab in the tag-on data acquisition sequence may have a small overlap with the imaging slab. The angle between the tagged slab and the imaging slab may be less than 30°.

In act 820, the MR system reconstructs a plurality of non-contrast MR images using the raw data in the region of interest (ROI). The MR system may use fast Fourier transforming (FFT) or other similar reconstruction algorithm to reconstruct the plurality of non-contrast MR images.

In act 830, the MR system obtains blood flow signals from the plurality of non-contrast MR images. The MR system may obtain blood flow signals including perfusion information by subtracting the tag-on image from the corresponding tag-off image at the same slice position. The blood flow signals in different imaging slices may be further analyzed. The blood signals at the same section may be further analyzed as a curve changing over time. The MR system may use the curve to identify a peak flow time. An example of the curve is shown in FIG. 9A-C.

In act 840, the MR system identifies an abnormal segment by analyzing the blood flow signals. The MR system may obtain a first threshold value corresponding to a peak blood flow in a normal tissue in an organ by receiving an input from an operator based on analyzing the non-contrast MR images as shown in act 854 of FIG. 12B. The MR system may also obtain a second threshold value corresponding to when the peak blood flow occurs in the normal tissue in the organ by analyzing non-contrast MR images. The MR system may then identify the abnormal segment by comparing the obtained blood flow signals to a threshold value corresponding to normal tissue in an organ as shown in act 856 of FIG. 12B.

Figure 8A:
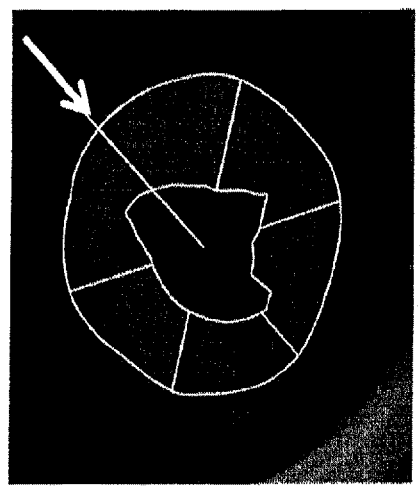
FIGS. 8A, 8B, 8C and 8D further depict an exemplary coronary artery territory segmentation in the left ventricle, here using an American Heart Association (AHA) six-segment model resulting in a color-mapped display of the segmented coronary artery territory of the left ventricle.
Figure 8B:
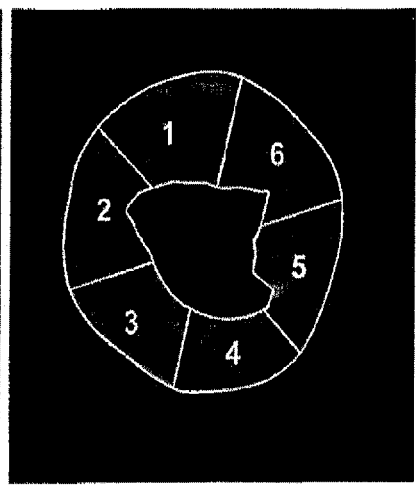
Figure 8C:
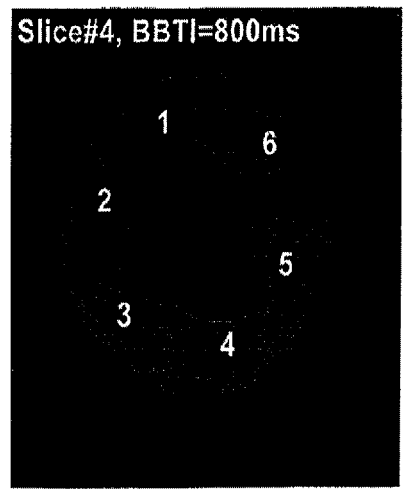
Figure 8D:
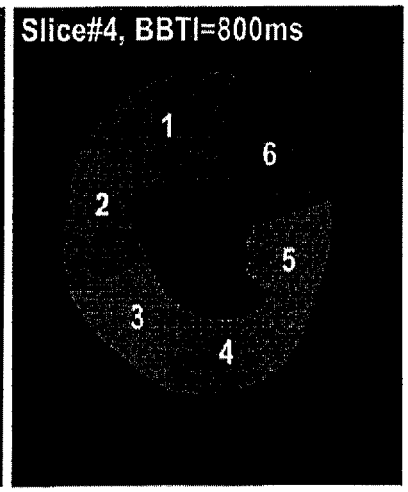

In act 850, the MR system displays the non-contrast MR images in a pop-up window by a highlighted segment to indicate the abnormal segment on the display. The MR system may superimpose a highlighted segment onto at least one non-contrast MR images to indicate the abnormal segment on the display. One of the examples of the display is similar to FIG. 8D, where the color map includes a particular highlight color to warn the operator about the abnormal segment. Note that FIGS. 7A and 7B may incorporate one or more superimposed images as shown in FIG. 8D to warn the operator about a particular segment before a treatment. After a treatment, the same ROI may be scanned and the same segment may be analyzed to determine whether the treatment is successful.

FIG. 12B illustrates the acts which may be combined with the acts in FIG. 12A. In act 852, the MR system may assign a first color to the highlighted segment to indicate a severity level of the abnormal segment on the display before the treatment. After the treatment, the MR system may assign a second color to the highlighted segment to indicate a successful treatment procedure.

In act 854, the MR system may obtain a first threshold value corresponding to a peak blood flow in a normal tissue in an organ by receiving an input from an operator based on analyzing the non-contrast MR images. The MR system may obtain a second threshold value corresponding to when the peak blood flow occurs in the normal tissue in the organ by analyzing non-contrast MR images. The first and second threshold values may be set based on inputs from operators by assuming most of tissue is normal and one or two segments are diseased. Alternatively or additionally, the first and second threshold values may be obtained using polynomial curve fitting.

In act 856, the MR system may identify an abnormal segment by comparing the obtained blood flow signals to a threshold value corresponding to normal tissue in an organ.

In act 858, the MR system may obtain a first plurality of blood flow signals corresponding to a region comprising abnormal tissue in an organ before a treatment procedure to restore perfusion in the region. The first plurality of plurality of blood flow signals may also be fitted using polynomial curve fitting to obtain one or more relevant fitted parameters.

In act 860, the MR system may obtain a second plurality of blood flow signals corresponding to the region comprising abnormal tissue in the organ after the treatment procedure. When the treatment is successful, the blood flow in the treated segment may have a higher blood flow compared to the normal tissue. Further, the peak time may also be shorter than the normal tissue. Thus, the MR system may combine both the peak flow and the peak time to determine whether the treatment is successful.

In act 862, the MR system may determine whether the treatment procedure is successful by comparing the first plurality of blood flow signals and the second plurality of blood flow signals. The MR system may obtain a second difference image by subtracting the first plurality of signals from the second plurality of signals to show the blood flow change before and after treatment.

In act 864, the MR system may determine that the treatment procedure is successful when the second plurality of blood flow signals indicate that a peak blood flow in the region is greater than a first threshold and a peak time corresponding to the peak blood flow is less than a second threshold. The MR system may report the determination result with peak blood flow and signal intensity with one or more corresponding non-contrast MR images to a diagnosis system connected to the MR system by a communication channel.

Not all acts shown in the flow charts of FIGS. 12A-B are required to be performed in each instance. One or more of the acts may be substituted by other acts disclosed in the disclosure. The acts may be combined with each other. Additional acts may be added when necessary.

The disclosure provides diagnostic tools for before treatment (screening) and after treatment (follow-up) of vascular disease using non-contrast MR sequences. Both infarction and revascularization may be observed in the time resolved blood flow signal acquired by a flow sensitive alternating inversion recovery (FAIR) and/or Time-Spatial Labeling Inversion Pulse (Time-SLIP) using tag-on (non-selective and selective IR pulses) and tag-off (non-selective IR pulse). Ischemic lesions may be also diagnosed by a delayed signal before the treatment and signal changes after treatment in 4D Time-SLIP method.

Further, the above changes before and after the treatment, may be highlighted in different colors for the lesion improvement, and the particular segment(s) may be shown in a pop-up to warn the doctors. The difference between normal, ischemia, and infarction before treatment, and the difference between normal, treated ischemia and treated infarction after revasculization, may be highlighted as well to warn the doctors. The peak signal time and peak under the curve area are recorded for relative blood flow signal under the various TIs. The area under the curve is checked before and after the treatment, which should be similar if tagged areas are the same in two scans.

The result of screening and follow up exam with peak blood flow and relative signal intensity is reported along with the images to support the diagnosis of diseases. Blood signals in different segments of organs, such as in lung, liver, kidney can be used to evaluate the stenosis level of blood vessel, and these results can be confirmed by the vessel morphology results using non-contrast magnetic resonance angiography (NC-MRA). Threshold values and blood traveling times may be different depending on the organs and tagged position. Other tagging condition such as Time-SLIP with tag-on (Selective IR pulse) and tag-off (no IR pulse) also may be used in this diagnostic tool. Blood signal in the segmentation of 6 or 17 AHA in myocardium may be used as compared to the vessel morphology using NC-MRA.

Other embodiments of the invention will be apparent to those skilled in the art from consideration of the specification and practice of the invention disclosed here. This application is intended to cover any variations, uses, or adaptations of the invention following the general principles thereof and including such departures from the present disclosure as come within known or customary practice in the art. It is intended that the specification and examples be considered as exemplary only, with a true scope and spirit of the invention being indicated by the following claims.

It will be appreciated that the present invention is not limited to the exact construction that has been described above and illustrated in the accompanying drawings, and that various modifications and changes can be made without departing from the scope thereof. It is intended that the scope of the invention only be limited by the appended claims.

What is claimed is:

1. A device for analyzing images from a magnetic resonance (MR) system, comprising:
   a hardware processor coupled with a storage system accessible to the hardware processor; and
   a display in communication with the at least one hardware processor,
   wherein the hardware processor is configured to
      receive a plurality of non-contrast MR images of a heart;
      obtain blood flow signals from the plurality of non-contrast MR images inside myocardium of the heart;
      obtain, by receiving input from an operator, a first threshold value corresponding to a peak blood flow in a first tissue in the heart and a second threshold value corresponding to when the peak blood flow occurs in the first tissue;
      identify, by comparing the blood flow signals to the first and second thresholds, a first spatial segment of the myocardium in which the obtained blood flow signals corresponding to the first tissue in the heart are below the first threshold value and for which the peak blood flow occurs after the second threshold value; and
      display on the display at least one of the non-contrast MR images with the first spatial segment of the myocardium highlighted as a highlighted spatial segment to indicate that the blood flow signals of the first spatial segment of the myocardium are below the first threshold value and have the peak blood flow value after the second threshold.

2. The device of claim 1, wherein the hardware processor is configured to:
   identify a plurality of second spatial segments of the myocardium in each of the plurality of non-contrast MR images;
   generate a curve as a function of a parameter indicating time for each second spatial segment, the curve indicating blood information in each segment; and
   calculate an area under the curve before a treatment to the first spatial segment of the myocardium and calculate an area under the curve after a treatment to the first spatial segment of the myocardium.

3. The device of claim 1, wherein the hardware processor is configured to obtain the first threshold value corresponding to the peak blood flow in the first tissue in the heart by receiving the input from the operator based on analyzing the non-contrast MR images.

4. The device of claim 1, wherein the hardware processor is configured to obtain a first plurality of the blood flow signals corresponding to a region in the heart before a treatment procedure to restore blood flow in the region.

5. The device of claim 4, wherein the hardware processor is configured to obtain a second plurality of the blood flow signals corresponding to the region after the treatment procedure.

6. The device of claim 5, wherein the hardware processor is configured to compare the first plurality of the blood flow signals and the second plurality of the blood flow signals.

7. The device of claim 6, wherein the hardware processor is configured to determine that the treatment procedure is successful when the second plurality of the blood flow signals indicate that the peak blood flow in the region is greater than the first threshold and a peak time corresponding to the peak blood flow is less than the second threshold.

* * * * *